US00PP15384P2

(12) United States Plant Patent
Olesen et al.

(10) Patent No.: US PP15,384 P2
(45) Date of Patent: Nov. 30, 2004

(54) ROSE PLANT NAMED 'POULHI014'

(50) Latin Name: *Rosa hybrid*
Varietal Denomination: POULhi014

(75) Inventors: L. Pernille Olesen, Fredensborg (DK); Mogens N. Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 0 days.

(21) Appl. No.: 10/812,741

(22) Filed: Mar. 29, 2004

(51) Int. Cl.[7] ..... A01H 5/00
(52) U.S. Cl. ..... Plt./122
(58) Field of Search ..... Plt./122

*Primary Examiner*—Anne Marie Grunberg
*Assistant Examiner*—Annette H Para

(57) ABSTRACT

A new garden rose plant of the miniature class which has abundant, orange-red flowers and attractive foliage. This new and distinct variety has shown to be uniform and stable in the resulting generations from asexual propagation.

1 Drawing Sheet

Botanical classification: *Rosa hybrid.*
Variety denomination: 'POULhi014'.

SUMMARY OF THE INVENTION

The present invention constitutes a new and distinct variety of garden rose plant which originated from a controlled crossing between the female parent, an un-named seedling, and the male parent, an un-named seedling. The two parents were crossed during the summer of 1992 and the resulting seeds were planted in a controlled environment in Fredensborg, Denmark. The new variety is named 'POULhi014'.

The new variety may be distinguished from its seed parent, an unnamed seedling, by the following combination of characteristics:

1. The seed parent has a taller growth habit than that of 'POULhi014'.
2. The seed parent, has larger flowers than those of 'POULhi014'.

The new variety may be distinguished from its male pollen parent, an un-named seedling, by the following characteristic. The pollen parent has dark red flowers, while 'POULhi014' has orange red flowers.

The objective of the hybridization of this rose variety was to create a new and distinct variety for garden use with unique qualities, such as:

1. Uniform and abundant orange-red flowers;
2. Vigorous, but compact growth when propagated both as a budded rose and on its own roots;
3. Disease resistance.

This combination of qualities is not present in previously available commercial cultivars of this type, known to the inventors, and distinguish 'POULhi014' from all other varieties of which we are aware.

As part of their rose development program, L. Pernille Olesen and Mogens N. Olesen germinated the seeds from the aforementioned hybridization during winter of 1992 and conducted evaluations on the resulting seedlings in a controlled environment in Fredensborg, Denmark.

'POULhi014' was selected in the spring 1993 by the inventors as a single plant from the progeny of the aforementioned hybridization.

Asexual reproduction of 'POULhi014' by traditional budding and rooted cuttings was first done by L. Pernille and Mogens N. Olesen in their nursery in Fredensborg, Denmark in July, 1993. This initial and other subsequent asexual propagations conducted in controlled environments have demonstrated that the characteristics of 'POULhi014' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, and stems, of 'POULhi014'. Specifically illustrated in the drawing:

FIG. 1.1; Open flower, stem showing open flowers, branching, and the attachment of leaves, buds, and peduncles;

FIG. 1.2; Flower bud closed, flower bud as sepals unfold, and partially open;

FIG. 1.3; Flower petals, detached;

FIG. 1.4; Sepals, receptacle, and peduncle;

FIG. 1.5; Juvenile and mature leaves;

FIG. 1.6; Bare stems.

DETAILED DESCRIPTION OF THE VARIETY

The following is a description of 'POULhi014', as observed in its growth in a field nursery in Jackson County, Oreg. Observed plants are 3 years of age and were grown on *Rosa multiflora* root stock. Color references are made using The Royal Horticultural Society (London, England) Colour Chart, 1995, except where common terms of color are used.

For a comparison, several physical characteristics of the rose variety 'POULhi005', a rose variety from the same inventors described and illustrated in U.S. Plant patent application Ser. No. 10/177,230 dated Jun. 21, 2002 are compared to 'POULhi014' in Chart 1.

CHART 1

| | 'POULhi014' | 'POULhi005 |
|---|---|---|
| Open flower general tonality | Red Group 44B with intonations of 45B | Red Group 45B |
| Petalage | 25 petals | 32 to 34 petals |
| Mature foliage color: upper surface | Green Group 137B | Green Group 137A |

FLOWER and FLOWER BUD

Blooming habit: Continuous.

Flower bud:

*Size.*—Upon opening, 15 to 18 mm in length from base of receptacle to end of bud. Bud diameter is 7 to 9 mm.

*Bud form.*—Short and pointed ovoid.

*Bud color.*—As sepals unfold, petals are Red Group 43B. At ¼ opening petals are Red Group 43A.

*Sepals.*—Upper Surface: Color: Yellow-Green Group 145A. Anthocyanic pigments the color of Greyed-Purple Group 184C to 184A. Surface: Surfaces of sepals moderately pubescent. Lower Surface: Color: Yellow-Green Group 144B. Anthocyanic pigments the color of Greyed-Purple Group 183A observed. Sepal Shape: Sepal apex is cirrhose. Base is flat at union with receptacle. Sepal Margin: Margins have strong foliaceous appendages on three of the five sepals. Stipitate glands are present in medium quantity. Size: 15 mm (l)×6 mm (w).

*Receptacle.*—Surface: Glaucous. Shape: Funnel shaped. Size: 4 mm (h)×5 mm (w). Color: Yellow-Green Group 144B. Anthocyanic pigments the color of Greyed-Purple Group 183D observed.

*Peduncle.*—Surface: Stipitate glands are very fragrant with a spicy scent. Length: 15 mm average length. Color: Yellow-Green Group 145B. Anthocyanic pigments the color of Greyed-Purple Group 183C observed. Strength: Somewhat strong.

*Borne.*—In clusters of 6 flower buds per stem.

Flower bloom:

*Fragrance.*—Light rose scent.

*Duration.*—The blooms have a duration on the plant of approximately 10 days. After flowers have completely matured, petals fall cleanly away from plant.

*Size.*—Flower diameter is 35 mm when open. Flower depth is 15 mm on average.

*Form.*—General shape is a rosette, Very double flower with many slightly overlapping petals. Shape of flower when viewed from the side: Upon opening, upper part: Flat. Upon opening, lower part: Flat. Open flower, upper part: Flattened convex. Open flower, lower part: Flat.

*Petalage.*—25 petals on average under normal conditions with 0 to 4 petaloids.

Color:

*Upon opening, petals.*—Outermost petals: Outer side: Red Group 42A. Inner Side: Red Group 40A to 42B. Innermost petals: Outer side: Red Group 42A. Inner Side: Red Group 44A.

*Upon opening, basal petal spots.*—Very distinctive. Outermost petals: Outer side: Yellow Group 6C. Inner Side: Yellow Group 6A. Innermost petals: Outer side: Yellow Group 6C. Inner Side: Yellow Group 6A.

*After opening, petals.*—Outermost petals: Outer side: Red Group 46C. Inner Side: Red Group 44B. Innermost petals: Outer side: Red Group 42A. Inner Side: Red Group 44A.

*Upon opening, basal petal spots.*—Very distinctive. Outermost petals: Outer side: Yellow Group 6C. Inner Side: Yellow Group 6A. Innermost petals: Outer side: Yellow Group 6C. Inner Side: Yellow Group 6A.

General tonality: On open flower Red Group 44B with intonations of 45B. No change in the general tonality at the end of the 10th day.

Petals:

*Petal reflex.*—Somewhat reflexed.

*Margin.*—Entire and uniform.

*Shape.*—Apex: Round. Base: Acute.

*Size.*—19 mm (l)×20 mm (w).

*Texture.*—Smooth.

*Thickness.*—Thin.

*Arrangement.*—Not Formal.

Petaloids:

*Quantity.*—0 to 4.

*Color.*—Upper Surface: Red Group 44A. Lower Surface: Red Group 42A.

*Size.*—12 mm (l)×4 mm (w).

*Shape.*—Base is acute. Apex is round.

Reproductive organs:

*Pistils.*—Length: 5 mm long. Quantity: 48 (actual count).

*Pollen.*—None observed.

*Anthers.*—Size: 1.50 mm in length. Color: Greyed-Orange Group 163B. Quantity: 63 (actual count).

*Filaments.*—Color: Yellow Group 3A. Length: 3 mm to 4 mm.

*Stigmas.*—Superior relative to the length of the filaments and the height of the anthers. Color: Greyed-Yellow Group 161C.

*Styles.*—Color: Greyed-Yellow Group 161D. Streaks of Red Purple Group 57A observed.

*Hips.*—None Observed in the field nursery.

PLANT

Plant growth: Compact and bushy. When grown as a budded field grown plant on *Rosa multiflora* understock, the average height of the plant is 40 cm to 60 cm. Average width is 40 cm.

Stems:

*Color.*—Young wood: Yellow-Green Group 144C. Older wood: Yellow-Green Group 144B to 144C.

*Surface texture.*—Young wood: Smooth. Older wood: Smooth.

Thorns:

*Incidence.*—0 to 1 thorn per 10 cm of stem.

*Size.*—Average length: 4 mm.

*Color.*—Greyed-Orange Group 176A.

*Shape.*—Concave.

Plant foliage: Normal number of leaflets on normal leaves in middle of the stem: 5 leaflets.

*Compound leaf size.*—75 mm (l)×50 mm (w).

*Color.*—Mature Foliage: Upper surface is: Green Group 137B. Lower surface is: Yellow-Green Group 147C. Juvenile foliage: Upper surface is: Green Group 137C. Lower surface is: Yellow-Green Group 147B. Anthocyanin: Location: Margins of juvenile foliage. Color: Greyed-Purple Group 184C.

Plant leaves and leaflets:

*Stipules.*—Size: 20 mm to 30 mm in length. Shape: Linear with outward extending apecies. Quantity: 2 per compound leaf. Margins: Medium stipitate glands. Color: Yellow Green Group 143A.

*Petiole.*—Length: 23 mm. Color: Yellow-Green Group 144C. Anthocyanic pigments Greyed-Red Group 181B observed. Texture: Smooth.

*Rachis.*—Length: 30 mm. Color: Yellow-Green Group 144C. Texture: Smooth.

*Leaflet.*—Edge: Finely serrated. Size: 31 mm (l)×21 mm (w). Shape: Generally ovate. Cuspidate leaf apecies. Leaf bases are rounded. Texture: Smooth. Thickness: Average. Arrangement: Odd pinnate. Venation: Reticulate. Glossiness: Moderately glossy.

Disease resistance: Above average resistance to mildew, rust, black spot, and *Botrytis* under normal growing conditions in Jackson County, Oreg.

Cold hardiness: The variety 'POULhi014' has been found to be cold tolerant to USDA Cold Hardiness Zone 6.

We claim:

1. A new and distinct variety of rose plant of the miniature rose class, substantially as herein illustrated and described as a distinct and novel rose variety due to its abundant orange-red flowers, disease resistance, and extended period of bloom.

* * * * *

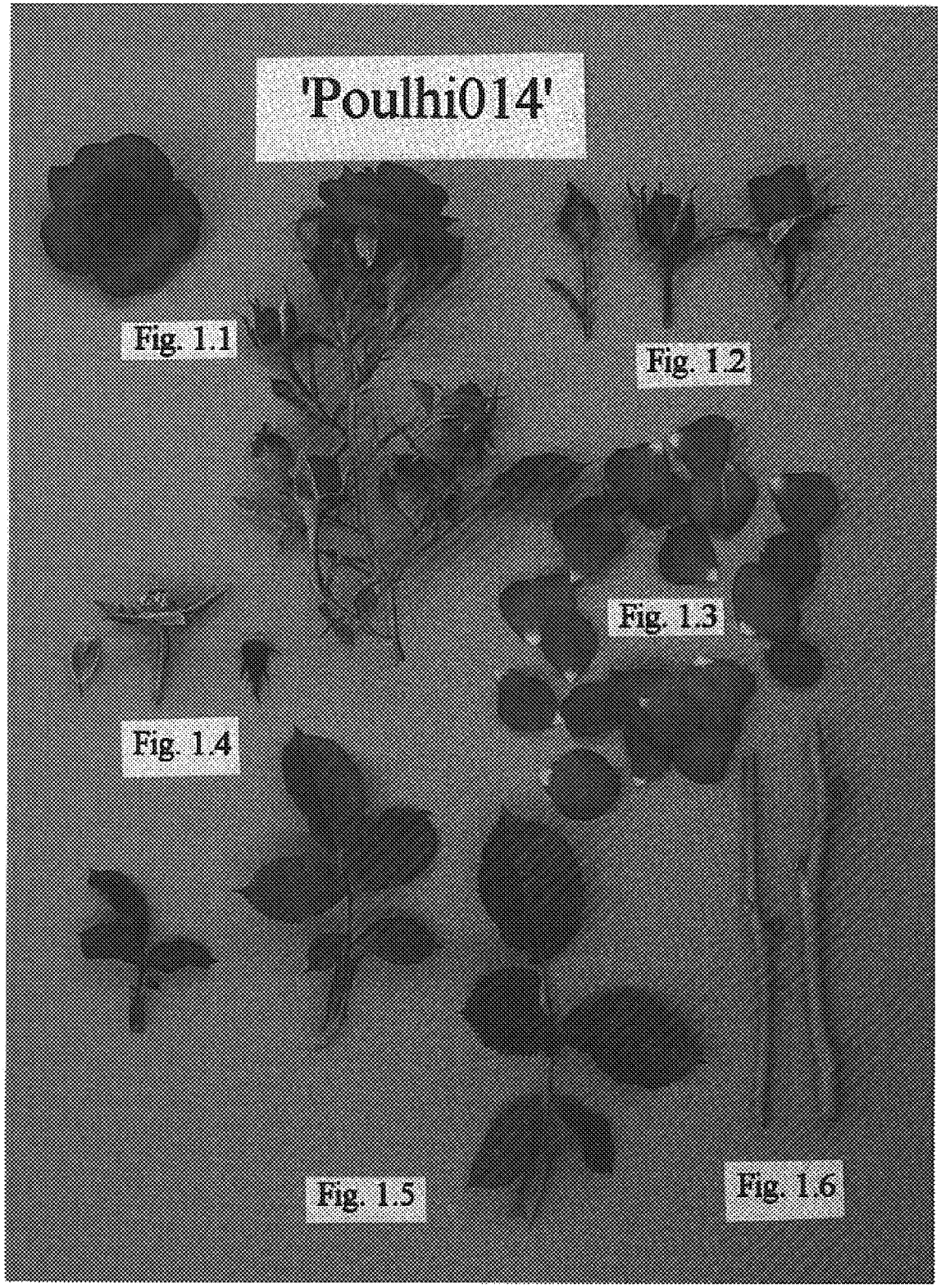
'Poulhi014'
Fig. 1.1
Fig. 1.2
Fig. 1.3
Fig. 1.4
Fig. 1.5
Fig. 1.6